(12) United States Patent
Tao et al.

(10) Patent No.: US 6,586,120 B2
(45) Date of Patent: Jul. 1, 2003

(54) ELECTRO LUMINESCENT DEVICE COMPRISING FLUORENE COMPOUNDS

(75) Inventors: Yu-Tai Tao, Taipei (TW); Chung-Wen Ko, Shijr (TW)

(73) Assignee: Academia Sinica, Taipei (TW)

( * ) Notice: Subject to any disclaimer, the term of this patent is extended or adjusted under 35 U.S.C. 154(b) by 73 days.

(21) Appl. No.: 09/846,639

(22) Filed: May 1, 2001

(65) Prior Publication Data

US 2002/0182439 A1 Dec. 5, 2002

(51) Int. Cl.$^7$ ........................ H05B 33/12; C07C 211/00
(52) U.S. Cl. ........................ 428/690; 428/917; 313/506; 313/504; 564/427; 564/428; 564/434; 548/440
(58) Field of Search ................................. 428/690, 917; 313/504, 506; 564/427, 308, 428, 434; 548/440

(56) References Cited

U.S. PATENT DOCUMENTS

| | | | |
|---|---|---|---|
| 5,698,740 A | 12/1997 | Enokida et al. | 564/308 |
| 6,180,217 B1 * | 1/2001 | Ueda et al. | 428/212 |
| 6,280,859 B1 * | 8/2001 | Onikubo et al. | 428/690 |

FOREIGN PATENT DOCUMENTS

JP             07-301928       * 11/1995

OTHER PUBLICATIONS

*Molecular Design of Hole Transport material with Various Ionization Potential for Organic Light–Emitting Diode Applications* by Satoshi Okutsu, Toshikazu Onikubo, Michiko Tamano, and Toshio Enokida. IEEE Transactions on Electron Devices, vol. 44, No. 8, Aug. 1997.
*Organic Electroluminescent Diodes* by C. W. Wang and S. A. Can Slyke. Applied Physics Letters vol. 51, No. 12, Sep. 21, 1987. pp. 913–915.
*The Electroluminescence of Organic Materials* by Ullrich Mitschke and Peter Bauerle. J. Mater. Chem., 2000, 10, pp. 1471–1507.
*Electroluminescence of Doped Organic Thin Films* by C. W. Tang, S. A. Van Slyke and C. H. Chen. Journal of Applied Physics, vol. 65, No. 9, May 1, 1999. pp. 3610–3616.
*Fabrication of Highly Efficient organic Electroluminescent Devices* by Junki Kido and Yasuhiro Iizumi. Applied Physics Letters, vol. 73, No. 19, Nov. 9, 1998. pp. 2721–2723.
*Observation of Crystallization of Vapor–deposited TPD Films by AFM and FFM* by Eun–mi Han, Lee–Mi Do, Yasuro Niidome, and Masamichi Fujihira. Chemistry Letters, 1994. pp. 969–972.
*Hole Transporting Materials with High Glass Transition Temperatures for Use in Organic Light–Emitting Devices* by Diarmuid F. O'Brien, Paul E. Burrows, Stephen R. Forrest, Bryan E. Koene, Douglas E. Loy and Mark E. Thompson. Advanced Materials, vol. 10, No. 14, 1998. pp. 1108–1112.
*Synthesis of Unsymmetrical Triarylamines for Photonic Applications via One–Pot Palladium–Catalyzed Aminations* by S. Thayumanavan, Stephen Barlow, and Seth R. Marder. Chem. Mater. Vol. 9, 1997. pp. 3231–3235.

* cited by examiner

Primary Examiner—Cynthia H. Kelly
Assistant Examiner—Dawn Garrett
(74) Attorney, Agent, or Firm—Fish & Richardson P.C.

(57) ABSTRACT

This invention relates to fluorene compounds and their use as a hole transport material in an electro-luminescence device.

8 Claims, No Drawings

ELECTRO LUMINESCENT DEVICE COMPRISING FLUORENE COMPOUNDS

BACKGROUND

Organic light emitting diodes (OLEDs) are attractive due to their potential use in a wide range of lightings as well as high and low resolution display applications. The simplest OLED device contains an organic emission layer sandwiched between two electrodes that inject electrons and holes. The electrons and holes meet in the organic emission layer and produce light. Multiple layers between the two electrodes can make the light production more efficient (Tang et al. (1987) *Applied Physics Letters* 51: 913–915, and Burroughs et al. (1990) *Nature* 347: 539). The multiple layers may include one or more electron transport layers, and one or more hole transport layers. See Adachi et al. (1988) *Japanese Journal of Applied Physics* 27: L269–L271, and Mitschke and Bäuerle (2000) *J. Mater. Chem.* 10: 1471–1507.

SUMMARY

This invention relates to compounds useful as a hole transport material in an OLED device.

In one aspect, the present invention features a fluorene compound having the formula:

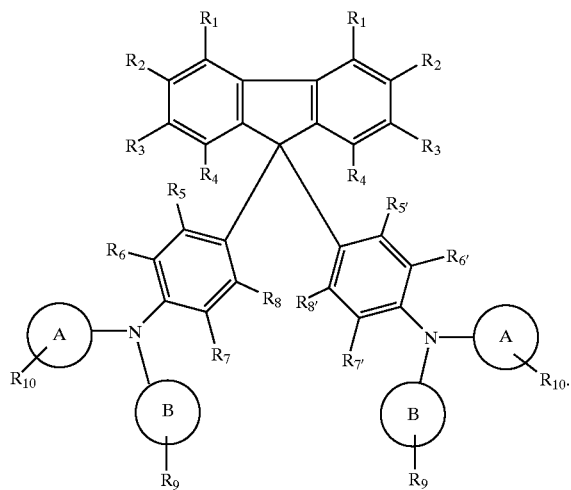

Each of $R_1$–$R_4$, $R_5$–$R_8$, and $R_{5'}$–$R_{8'}$, independently, is H, halogen, CN, $NO_2$, amino, alkylamino, arylamino, dialkylamino, diarylamino, hydroxyl, alkoxyl, aryloxyl, heteroaryloxyl, mercapto, alkylthio, arylthio, heteroarylthio, alkyl, aryl, heteroaryl, or heterocyclyl; each of A and B, independently, is phenyl, naphthyl, or phenanthryl; and each of $R_9$ and $R_{10}$, independently, is H, aryl, heteroaryl, aryloxyl, or heteroaryloxyl; provided that if both A and B are phenyl, then one of $R_9$ and $R_{10}$ is not H. Note that if each of $R_5$–$R_8$ is the same as each of $R_{5'}$–$R_{8'}$, correspondingly, the compounds of this invention are symmetrical. Further, $R_9$ or $R_{10}$ can be substituted at any suitable position on ring B or A. A subset of the compounds encompassed by the above formula are featured by that each of $R_9$ and $R_{10}$, independently, is H, aryl, or heteroaryl. In these compounds, each of A and B, independently, can be phenyl or naphthyl, and each of $R_1$–$R_4$, $R_5$–$R_8$, and $R_{5'}$–$R_{8'}$, independently, is H, dialkylamino, diarylamino, alkyl, aryl, or heteroaryl.

Alkylamino, arylamino, dialkylamino, diarylamino, alkoxyl, aryloxyl, heteroaryloxyl, alkylthio, arylthio, heteroarylthio, alkyl, aryl, heteroaryl, heterocyclyl, phenyl, naphthyl, and phenanthryl mentioned above include both substituted and unsubstituted moieties. The term "substituted" refers to one or more substituents (which may be the same or different), each replacing a hydrogen atom. Examples of substituents include, but are not limited to, halogen, amino, alkylamino, arylamino, dialkylamino, diarylamino, hydroxyl, mercapto, cyano, nitro, $C_1$–$C_6$ alkyl, $C_1$–$C_6$ alkenyl, $C_1$–$C_6$ alkoxy, aryl, heteroaryl, or heterocyclyl, wherein alkyl, alkenyl, alkoxy, aryl, heteroaryl, and heterocyclyl are optionally substituted with $C_1$–$C_6$ alkyl, halogen, amino, alkylamino, arylamino, dialkylamino, diarylamino, hydroxyl, mercapto, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, pyridinyl, carbazolyl, and indolyl.

One exemplary compound of this invention is 9,9-bis{4-[di-(p-biphenyl)aminophenyl]}fluorene (BPAPF):

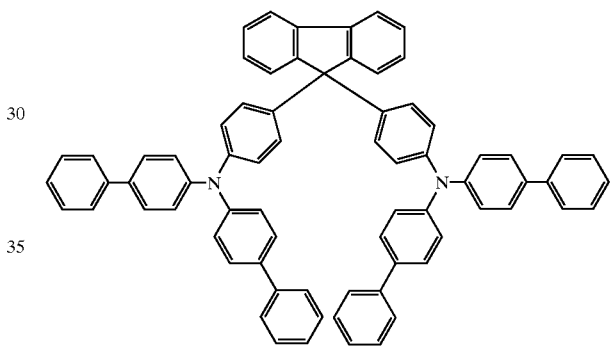

Also within the scope of this invention is an electroluminescence device made with one or more of the fluorene compounds described above. The device includes an anode layer; a hole transport layer that can include the fluorene compounds of this invention; an electron transport layer; and a cathode layer. The anode, the hole transport layer, the electron transport layer, and the cathode are disposed in the above order.

The details of one or more embodiments of the invention are set forth in the description below. Other features, objects, and advantages of the invention will be apparent from the description and from the claims.

DETAILED DESCRIPTION

This invention relates to fluorene compounds and their use as a hole transport material in an electro-luminescence device.

The fluorene compounds of this invention can be prepared by methods well known to a skilled person in the art, including the synthetic routes disclosed herein.

For example, shown below is a scheme that depicts synthesis of a symmetrical compound (right) and an asymmetrical compound (left) from a starting material such as fluorenone:

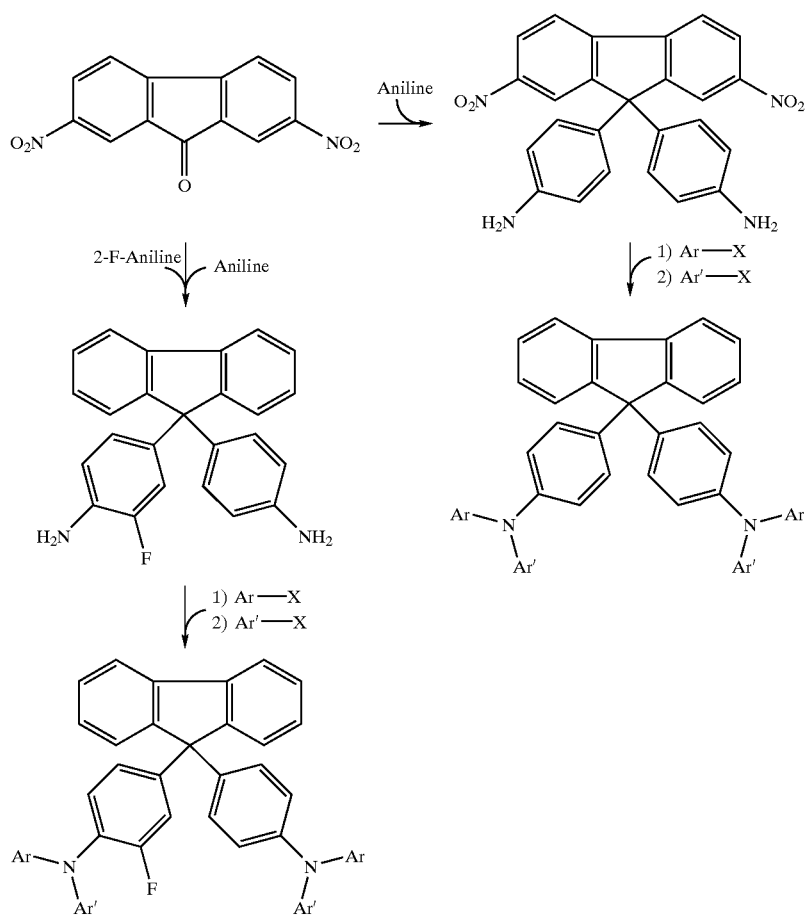

More specifically, a symmetrical compound can be synthesized by the following method: A mixture containing a fluorenone and an aniline is refluxed in the presence of an acid catalyst to produce an intermediate 9,9-bis(aminophenyl)fluorene. The intermediate is subsequently reacted with aryl halides (Ar—X and Ar'—X, stepwise) in the presence of a catalyst such as palladium to obtain the desired symmetrical product. An asymmetrical compound, on the other hand, can be synthesized as follows: A reaction mixture containing a fluorenone and two different anilines (e.g., an aniline and a 2-fluoroaniline as shown in the above scheme) is refluxed in the presence an acid catalyst to produce a mixture including an asymmetric fluorene intermediate. The asymmetric fluorene intermediate is then reacted with aryl halides (Ar—X and Ar'—X, stepwise) in the presence of a catalyst such as palladium to produce the desired asymmetrical product.

As another example, a scheme below depicts synthesis of other compounds of this invention from a different starting material such as a dinitro-substituted fluorenone:

2,7-Bis(diarylamino)-9,9-bis(diarylaminophenyl) fluorene, a compound of this invention, can be synthesized according to the above synthetic route as follows: A mixture of a 2,7-dinitrofluorenone and an aniline is refluxed in the presence of an acid catalyst to give an intermediate 2,7-dinitro-9,9-bis(aminophenyl)fluorene. The two nitro groups are then converted to two amino groups by a reduction reaction with $Fe/NH_4Cl$. Finally, the reduced intermediate is reacted with aryl halides (Ar—X and Ar'—X, stepwise) in the presence of a catalyst such as palladium to produce the desired product.

BPAPF can be prepared by the method described above. It can also be prepared as follows: A reaction mixture containing commercially available 9, 9-bis(4-aminophenyl) fluorene and 4-bromobiphenyl in toluene is refluxed for 20 hr in the presence of a catalytic amount of $Pd_2(dba)_3$, 1,10-phenanthroline, and potassium hydroxide. After cooling, the reaction mixture is filtered and washed with $H_2O$ and ethyl acetate. The solid is collected and purified by sublimation.

The compounds of the invention can be used as a hole transport material in an electro-luminescence device.

Typically, the electro-luminescence device can be classified as a two-layer structured device or a three-layer structured device. A two-layer structured device can include a hole transport layer and an electron transport layer, both of which are sandwiched between a pair of electrodes. The electron transport layer can function as a luminescent layer, which transports electrons and emits lights (Tang et al., (1989) *J. Appl. Phys.* 65: 3610). Generally, a hole transport layer, an electron transport layer, and a cathode layer are deposited sequentially in the above order. The anode layer can be formed on a substrate, such as a glass. A three-layer structured device can include an anode layer, a hole transport layer, a luminescent layer and an electron transport layer, and a cathode layer in the above order. The luminescent layer can be another hole transport or another electron transport layer.

Optionally, the electro-luminescence device can include a dopant-containing layer, which can be an electron transport layer or a luminescent layer. The dopant-containing layer can also be located within the electron transport layer or the luminescent layer, or can be sandwiched between one of the just-mentioned layers and a neighboring layer.

Each of the above mentioned layers can be made of various materials, as described in, for example, U.S. Pat. No. 5,698,740. More specifically, a substrate can be made of, e.g., glass; an anode layer can be a film of a transparent electroconductive material, e.g., indium tin oxide (ITO), formed on the substrate; a hole transport layer can be made of, e.g., 4,4'-bis[N-(1-naphthyl)-N-phenyl-amino]-biphenyl (NPB) or a compound of this invention, formed on the anode layer; an electron transport layer can be made of, e.g., tirs(8-quinolinolate)aluminum ($Alq_3$), deposited on the hole transport layer; and a cathode layer can be made of a metal film, e.g., an alloy of magnesium and silver. The dopant-containing layer can be made of one or more organic fluorescent molecules, e.g., quinacridone.

The fabrication of an electro-luminescence device has been described in, for example, Tang & VanSlyke (1987) *Appl. Phys. Lett.* 51: 913; Tang et al., (1989) *J. Appl. Phys.* 65: 3610, or Kido & Lizumi (1997) *Chem. Lett.* 963. More specifically, each layer may be formed by any one of film forming methods such as vacuum deposition. See U.S. Pat. No. 5,698,740.

Unexpectedly, the compounds of this invention, such as BPAPF, have excellent thermal stability and electrochemical stability, being quantified by parameters such as glass transition temperature (Tg), single oxidation potential (Vo), crystallizing temperature (Tc), or melting temperature (Tm). For example, BPAPF has a Tg of 167° C., a Vo of 0.95V, a Tc of 288° C., and a Tm of 327° C. In contrast, NPB has a Tg of ~100° C. and a Vo of 0.83V. See, e.g., O'Brien et al. (1998) *Adv. Mater.* 10: 1108 or Koene et al. (1998) *Adv. Mater.* 10: 2235.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Fabrication of Non-doped Devices using BPAPF as a Hole Transport Material

A two-layer structured device was fabricated on an ITO coated glass substrate (as an anode) by sequentially depositing 40 nm of BPAPF as a hole transport layer, 40 nm of $Alq_3$ as an electron transport layer, and 50 nm of an alloy of Mg—Ag (10:1) as a cathode layer. The device was then capped with 100 nm of Ag metal. A device using NPB as the hole transport layer was also prepared. A bright green emission (520 nm) from the $Alq_3$ layer was observed in both cases.

In addition, devices were prepared of different thicknesses of BPAPF and $Alq_3$, e.g., a device including 50 nm of BPAPF and 50 nm of $Alq_3$ and a device including 60 nm of BPAPF and 50 nm of $Alq_3$. See Table 1.

The performance of the devices can be characterized by parameters such as turn-on voltage (V), luminance ($Cd/m^2$), maximum luminance ($Cd/m^2$), luminance efficiency (Cd/A), external quantum efficiency (%), and power efficiency (%), measured on a Keithley 2400 Source meter, a Newport 1835C optical meter equipped with a Newport 818-ST silicon photodiode. See Table 1.

The current-voltage-luminance (I-V-L) characteristics were also measured. The luminance and external quantum efficiency of each of the BPAPF-containing devices were always better than those of the NPB-containing devices.

A three-layer structured device was also fabricated on an ITO coated glass substrate (as an anode) by sequentially depositing 60 nm of BPAPF as a hole transport layer, 10 μm of dipyrazolopyridine (PAP-Ph) as a luminescent layer, 30 nm of $Alq_3$ as an electron transport layer, and 50 nm of an alloy of Mg—Ag (10:1) as a cathode layer. A device including 40 nm of NPB as the hole transport layer was also prepared. As shown in Table 1, the BPAPF-containing device had higher luminance efficiency and external quantum efficiency than the NPB-containing device.

TABLE 1

Device Characteristics for LED fabricated (at a current density of 100 mA/cm$^2$)

| Device Structure | Voltage (V) | Luminance (Cd/m$^2$) | Maximum Luminance (Cd/m$^2$) | Luminance Efficiency (Cd/A) | Quantum Efficiency (%) | Power Efficiency (1 m/W) |
|---|---|---|---|---|---|---|
| NPB(40 nm)/Alq(40 nm) | 6.1 | 2776 | 30129 | 2.76 | 1.07 | 1.42 |
| BPAPF(40 nm)/Alq(40 nm) | 5.2 | 3638 | 34290 | 3.64 | 1.20 | 2.21 |
| BPAPF(50 nm)/Alq(50 nm) | 8.0 | 5252 | 42257 | 5.25 | 1.82 | 2.07 |
| BPAPF(60 nm)/Alq(50 nm) | 7.2 | 5646 | 49287 | 5.63 | 2.01 | 2.45 |
| NPB(90 nm)/Alq:QD(20 nm)/Alq(30 nm) | 7.8 | 6385 | 63431 | 6.42 | 3.11 | 2.59 |
| BPAPF(60 nm)/Alq:QD(20 nm)/Alq(30 nm) | 7.2 | 12891 | 139550 | 12.90 | 3.89 | 5.60 |
| NPB(90 nm)/Alq:C6(20 nm)/Alq(30 nm) | 7.2 | 4180 | 35414 | 4.18 | 1.45 | 1.83 |
| BPAPF(60 nm)/Alq:C6(20 nm)/Alq(30 nm) | 6.9 | 5608 | 52491 | 5.62 | 2.01 | 2.57 |
| NPB(90 nm)/Alq:DCM(20 nm)/Alq(30 nm) | 6.9 | 1004 | 8552 | 1.01 | 0.67 | 0.46 |
| BPAPF(60 nm)/Alq:DCM(20 nm)/Alq(30 nm) | 7.6 | 1163 | 9760 | 1.17 | 0.85 | 0.48 |
| NPB(40 nm)/PAP-Ph(10 nm)/Alq(30 nm) | 7.3 | 1293 | 10492 | 1.30 | 0.91 | 0.56 |
| BPAPF(60 nm)/PAP-Ph(10 nm)/Alq(30 nm) | 7.6 | 2239 | 15994 | 2.24 | 1.37 | 0.92 |

EXAMPLE 2

Fabrication of Doped Devices including BPAPF as a Hole Transport Material

A dopant-containing device was fabricated on an ITO coated glass substrate (as an anode) by sequential deposition of 60 nm of BPAPF as a hole transport layer, 20 nm of Alq$_3$ doped with ~0.5% of quinacridone (QD) and 30 nm of Alq$_3$ as an electron transport layer, and 50 nm of an alloy of Mg—Ag (10:1) as a cathode layer. A device using 90 nm of NPB as the hole transport layer was also prepared. Unexpectedly, the device having a BPAPF-hole transport layer had much higher luminance (~140,000 Cd/M2 at 15 V) than that using NPB as the hole transport layer (~63,000 Cd/m$^2$ at 15 V). The maximum external quantum efficiency of the BPAPF-containing device was also higher (4.1% at 5.5 V) than that of the NPB-containing device (3.3% at 6 V). The BPAPF-containing device showed a maximum power of 10.0 1 m/W at 4.5 V and a luminance efficiency of this device was 13.7 Cd/A at 5.5 V, double those shown by the NPB-containing device (i.e., 4.3 lm/W at 4.5 V and 6.9 Cd/A at 6.0V).

Two additional dopant-containing devices were also fabricated. In these two devices, the above-mentioned doped layer was replaced with 20 nm of Alq$_3$ doped with 1% coumarin 6 (C6), or 20 nm of Alq$_3$ doped with 0.5% of 4-(dicyanomethylene)-2-methyl-6-(4-dimethylamino-styryl)-4H-pyran (DCM). Devices including 60 nm of BPAPF and 90 nm of NPB, respectively, as the hole transport layer were prepared. As shown in Table 1, the luminance and external quantum efficiency of each of the BPAPF-containing devices were higher than those of the NPB-containing devices.

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. An electro-luminescence device for emitting light within a visible light wavelength, comprising:
   an anode layer;
   a hole transport layer
   an electron transport layer; and
   a cathode layer;
   wherein the anode layer, the hole transport layer, the electron transport layer, and the cathode layer are disposed in the above order; and the hole transport layer includes a compound having the formula:

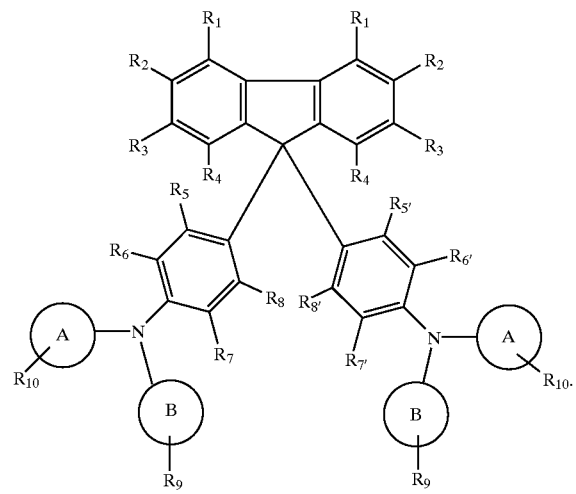

in which
each of $R_1$–$R_4$, $R_5$–$R_8$, and $R_{5'}$–$R_{8'}$, independently, is H, halogen, CN, NO$_2$, amino, alkylamino, arylamino, dialkylamino, diarylamino, hydroxyl, alkoxyl, aryloxyl, heteroaryloxyl, mercapto, alkylthio, arylthio, heteroarylthio, alkyl, aryl, heteroaryl, or heterocyclyl;
each of A and B, independently, is phenyl, naphthyl, or phenanthyl; and
each of $R_9$ and $R_{10}$, independently, is aryl, heteroaryl, aryloxyl, or heteroaryloxyl.

2. The device of claim 1, wherein each of $R_9$ and $R_{10}$, independently, is aryl or heteroaryl.

3. The device of claim 2, wherein each of A and B, independently, is phenyl or naphthyl.

4. The device of claim 3, wherein each of $R_1$–$R_4$, $R_5$–$R_8$, and $R_{5'}$–$R_{8'}$, independently, is H, dialkylamino, diarylamino, alkyl, aryl, or heteroaryl.

5. The device of claim 4, wherein each of $R_1$–$R_4$, $R_5$–$R_8$, and $R_{5'}$–$R_{8'}$, independently, is H, dialkylamino, or diarylamino.

6. The device of claim 2, wherein each of $R_1$–$R_4$, $R_5$–$R_8$, and $R_{5'}$–$R_{8'}$, independently, is H, dialkylamino, diarylamino, alkyl, aryl, or heteroaryl.

7. The device of claim 6, wherein each of $R_1$–$R_8$, and $R_{5'}$–$R_{8'}$, independently, is H, dialkylamino, or diarylamino.

8. The device of claim 1, wherein the compound is:

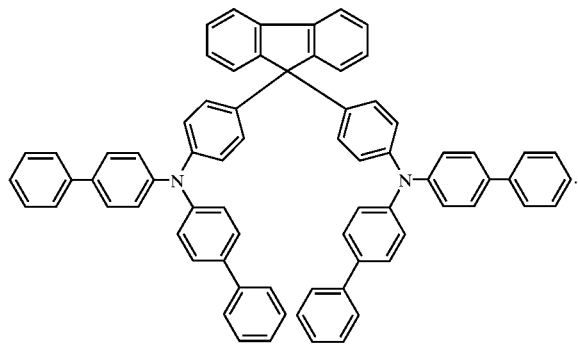

* * * * *